(12) United States Patent
Possover (10) Patent No.: US 10,232,175 B2
(45) Date of Patent: Mar. 19, 2019

(54) RETROPUBIC IMPLANTATION OF A MICROSTIMULATOR FOR GENITAL NERVES STIMULATION

(71) Applicant: Marc Possover, Hagendorn (CH)

(72) Inventor: Marc Possover, Hagendorn (CH)

(*) Notice: Subject to any disclaimer, the term of this patent is extended or adjusted under 35 U.S.C. 154(b) by 0 days.

(21) Appl. No.: 15/189,248

(22) Filed: Jun. 22, 2016

(65) Prior Publication Data
US 2017/0368340 A1    Dec. 28, 2017

(51) Int. Cl.
*A61N 1/36*     (2006.01)
*A61N 1/05*     (2006.01)
*A61N 1/372*    (2006.01)

(52) U.S. Cl.
CPC ....... *A61N 1/36007* (2013.01); *A61N 1/0521* (2013.01); *A61N 1/0558* (2013.01); *A61N 1/36107* (2013.01); *A61N 1/37205* (2013.01); *A61N 1/37247* (2013.01)

(58) Field of Classification Search
CPC ............ A61N 1/36007; A61N 1/37247; A61N 1/37205; A61N 1/0558; A61N 1/0521; A61N 1/36107
See application file for complete search history.

(56) References Cited

U.S. PATENT DOCUMENTS

| | | | | |
|---|---|---|---|---|
| 4,585,005 A | * | 4/1986 | Lue | ................... A61N 1/36007 607/39 |
| 7,006,870 B1 | * | 2/2006 | Whitehurst | ........ A61N 1/36007 607/143 |
| 2006/0129028 A1 | * | 6/2006 | Krakousky | ........ A61N 1/36007 600/40 |

\* cited by examiner

*Primary Examiner* — Rex R Holmes
(74) *Attorney, Agent, or Firm* — Bachman & LaPointe, PC (57) ABSTRACT

A method for implanting a stimulator for genital nerves stimulation, including approaching the genital nerves of a patient, defined as the dorsal nerve of the penis/clitoris (DNP), the cavernous nerve (CN) or both the DNP and CN, ventrally by way of the retropubic space to implant a stimulator to contact the genital nerves in this location; and controlling the stimulator to influence at least one of the genital nerves.

8 Claims, 5 Drawing Sheets

FIG. 4
Parasympathetic (carvernous nerve) and somatic (dorsal penis nerve) of the genital organ in men

FIG. 5

RETROPUBIC IMPLANTATION OF A MICROSTIMULATOR FOR GENITAL NERVES STIMULATION

BACKGROUND OF THE INVENTION

Urinary incontinence, bladder overactivity, sexual dysfunction, and other pelvic floor disorders are common problems affecting people of all ages, gender and race.

Overactive bladder (OAB) is a condition that affects millions of citizens worldwide. OAB is a urological condition defined by a set of symptoms: urgency, with or without urge incontinence, usually with frequency and nocturia. Frequency is usually defined as urinating more than 8 times a day. Symptoms of OAB can include urinary frequency, urinary urgency, and urinary urge incontinence due to a sudden and unstoppable need to urinate, nocturia or enuresis resulting from overactivity of the detrusor muscle. The major symptom of OAB is a "gotta go" feeling, —the sudden, strong urge to urinate that the patient can't control. Sometimes people with OAB also have "urgency incontinence". This means that urine leaks after they feel the sudden urge to go. Carrying out the activities of daily life and engaging in social and occupational activities can be profoundly affected by lack of bladder control and incontinence. OAB may cause significant social, psychological, occupational, domestic, physical, and sexual problems, with social and professional isolation.

Urinary incontinence is defined as an involuntary loss of urine. Women experience this condition twice as often as men. Pregnancy and childbirth, menopause, and the structure of the female urinary tract account for this difference. Both women and men can become incontinent from neurologic injury, birth defects, stroke, multiple sclerosis, and physical problems associated with aging. The US Department of Health and Human Services estimates that approximately 13 million Americans suffer from urinary incontinence. Urinary incontinence is an underdiagnosed and underreported problem that increases with age, affecting 50-84% of the elderly in long-term care facilities. Urinary incontinence is at any age more than 2 times more common in females than in males. 10% to 30% of American women/girls aged 15-64 years are thought to suffer from it, compared to between 1.5% and 5% of men. Over half of all nursing home residents are thought to be affected by urinary incontinence. It is estimated that 20% of all women over the age of 40 are affected by urinary incontinence.

Sexual dissatisfaction and/or trouble with penis/clitoris erection affects both women and men. In men, erectile dysfunction is the inability to achieve and sustain an erection suitable for sexual intercourse. Occasional erectile dysfunction are not uncommon. Many men experience it during times of stress. It can also be a sign of emotional or relationship difficulties that may need to be addressed by a professional. Up to 30 million American men are affected by erectile dysfunction. Risk for such sexual dysfunction in men increases with age. Women's sexual health, like men's, is important to overall emotional and physical well-being. Many people think that sexual activity is motivated by physical desire, such as the desire of the body to want sex, which leads to sexual arousal and then orgasm. Although this may be true for men, research suggests that women's sexual motivations and responses may be more complex. For many women, particularly those who are older than 40 or who have gone through menopause, physical desire isn't the primary motivation for sex. What it means to be sexually satisfied may differ for men and women, and even among women. Some women say the pleasure of sexual arousal is sufficient, while others want to experience orgasm.

The three most common sexual dysfunctions in males are decreased libido, erectile dysfunction (ED) and ejaculatory dysfunction. ED is a common problem in primary care and currently affects more than 150 million men worldwide, with a projected prevalence increase to 322 million men by the year 2025. ED has a significant impact on patient's quality of life, self-confidence and interpersonal relations. The safety and efficacy of phosphodiesterase 5 (PDE5) inhibitors has been well documented. First-line therapy for treatment of ED is medication with a PDE5 inhibitor. A contraindication for the use of PDE5 inhibitors is the intake of nitrates, and patients with severe cardiovascular comorbidities should not use a PDE5 inhibitor. Up to 50% of patients suffering from ED present a suboptimal answer to the PDE5 inhibitors. During recent years, downsizing of catheter material has facilitated endovascular revascularization of small-caliber erection-related arteries.

In a study known as the ZEN study (Rogers J H, Goldstein I, Kandzari D E, Kohler T S, Stinis C T, Wagner P J, et al. *Zotarolimus-eluting peripheral stents for the treatment of erectile dysfunction in subjects with suboptimal response to phosphod-iesterase-5 inhibitors*, J Am Coll Cardiol. 2012; 60(25):2618-27), procedural success was 100% with no major adverse events during follow-up. About 60% of patients undergoing stent placement showed functional improvement subsequent to endovascular revascularization. However, the restenosis rate was reported to be as high as 34% in these small-caliber arteries after 6 months of follow-up.

Electrical stimulation of pelvic nerves in the pelvic floor may provide an effective therapy for a variety of disorders. Electrical stimulation has emerged as an alternative and attractive treatment for refractory cases of bladder overactivity, urinary incontinence and also bladder retention (incapacity of bladder voiding). In urinary incontinence and bladder overactivity, because the stimulation of the pudendal nerve induces a relaxation of the bladder muscle, and a contraction/closure of the urethral sphincter, it aids the patient in reducing unwanted urinary voiding, and pain due to overactive bladder. Also the stimulation may be effective in restoring sexual function or alleviating pelvic floor or genital pain.

Stimulation leads are ordinarily implanted surgically or percutaneously.

Sacral nerve stimulation enables stimulation of pudendal fibers—the key player of the functions of the pelvic organs including the genital organs—contained in the sacral nerve root, and also activates other fibers that are present in the sacral nerve root. This in turn produces some patient discomfort such as feeling of electricity in the leg. Also because the fibers of the pudendal nerve are dispatched between the sacral nerve roots S2, S3 and S4, only stimulation of all three roots together can reach all pudendal fibers together. However in the actual form of sacral nerve stimulation, a technique called Interstim—Medtronic, one lead can only stimulate one nerve.

Pudendal nerve stimulation includes stimulation of active sensoric and motoric fibers designed for the urinary bladder, the rectum, the sexual organs and both the anal and urethral sphincters. Neuromodulation of the pudendal nerve enables optimal control of bladder overactivity, fecal and urinary incontinence—especially in combination. The "pudendal LION Procedure" permits the implantation of a lead at the origin of the nerve at the level of the less sciatic notch via a laparoscopic approach. This approach also permits a selective exposure of the dorsal nerve of the clitoris/penis but the dissection is laborious, requiring transection of the sacrospinal ligament and an absolute expertise in laparoscopic advanced neuropelveological surgery. All further techniques of implantation of a lead to the pudendal nerve are based on the percutaneous implantation below the pelvic floor. So the transobturator procedure (Transobturator lead implantation for pelvic floor stimulation—Siegel—US Patent 2007/0173900) permits implantation of a lead electrode by percutaneous implantation technique to the pudendal nerve or even to the dorsal nerve of the penis/clitoris (DNP) below the pelvic diaphragm, close to the ischium in proximity to the sciatic spine where the nerve emerges from the pudendal nerve (Abb 1-2). Because the lead cannot be fixed to any anatomical structures, such techniques of implantation below the pelvic floor always expose the patient to risk of electrode breakage, dislocation and migration.

Because part of the DNP lies superficially to the skin outside the pelvis, this nerve can be stimulated using surface electrodes attached to the overlying skin. This application is also limited due to intolerance to the required high stimulation amplitude. In patients with intact sensitivity, this leads to stimulation amplitudes that are less effective or too low to be effective, which subsequently results in incontinence. Surface electrodes have additional limitations such as difficulties in daily proper placement and hygiene.

Implanted electrodes are more suitable, but implanted electrodes in the penis or near the clitoris have to endure mechanical stress of penile erections and external pressure, with risk for cable/electrode breakage and dislocation.

A technique for percutaneous implantation of an electrode near the origin of the DNP close to the Alcock's canal have also been developed. Because such technique lacks direct vision to the nerve during implantation, X-ray screening and neuro-physiological monitoring of the nerve are usually mandatory. The technique is not easy and also exposes patients to electrode migration and failure since the lead is not fixed to any anatomical structure and patients are sitting on the lead.

Providing a controlled and sustained penile erection for a disabled patient also includes stimulation of the cavernous nerves (CN), which nerves contain major genital parasympathetic fibers (Eckhard, Untersuchung über die Erektion des Penis beim Hunde. Beiträge zur Anat. Und Physiologie, vol iii, Giessen 1863). Stimulation of the CN produces a sustained reflex erection by increasing filling of the penis via dilatation of penile arteries, and at the same time preventing leakage via occlusion of penile veins. Pelvic sympathetic nerves are theoretically responsible for detumescence, but electrical stimulation of the sympathetic pathways to the penis also may produce erection (K-E Andersson, P Hedlund, P Alm2. Symptahetic pathways and adregernic innervation of the penis. Int. J. of Impotence Research 2000; 12, Suppl 1:5-12). The classical location for electrode placement is at the inferior hypogastric plexus close to the apex of the prostate. However, this technique requires surgical exposure of the pelvic plexus, the lateral bladder and rectal wall and the inferior hypogastric plexus and intraoperative neuronavigation for identifying the bundle of cavernous nerves.

None of the previous techniques permit an approach to the dorsal nerve of the penis/clitoris or to the cavernous nerves, or to the genital sympathetic nerves below the pubic arch (which is anatomically not feasible) where the nerve passes down to the sexual organs. Further, a percutaneous approach coming from lateral or dorsal to the location of the nerve below the pubic bone would expose the patient to high risk of damage to the deep dorsal vein and to the lateral venous plexus with, as a consequence, massive hemorrhaging and risk of death.

None of the above mentioned methods enable bilateral and concomitant stimulation of the genital nerves. Unilateral stimulation may induce a unilateral erection and deviation of the penis in men.

SUMMARY OF THE INVENTION

According to the invention, a method for implanting a stimulator for genital nerves stimulation is provided, comprising: approaching genital nerves of a patient, defined as the dorsal nerve of the penis/clitoris (DNP), the cavernous nerves (CN) or both the DNP and CN, ventrally by way of the retropubic space to implant a stimulator to contact the genital nerves in this location; and controlling the stimulator to influence at least one of the genital nerves.

Following this approach, stimulation of the genital nerves is accomplished in a way which has little or no risk of migration of the device, and the method is simple and easy, as is use of the device.

BRIEF DESCRIPTION OF THE DRAWINGS

A detailed description of preferred embodiments of the invention follows with reference to the attached drawings, wherein.

DETAILED DESCRIPTION

According to the invention, and from an anatomical point of view, the only safe and reasonably easy way to reach the dorsal nerve of the penis/clitoris, the cavernous nerves and the genital sympathetic nerves all together by a single approach without risk of damage to the above mentioned vessels is to enter ventrally by passing through the retropubic space of Retzius. The presented technique is based on this new approach.

Figure 1:
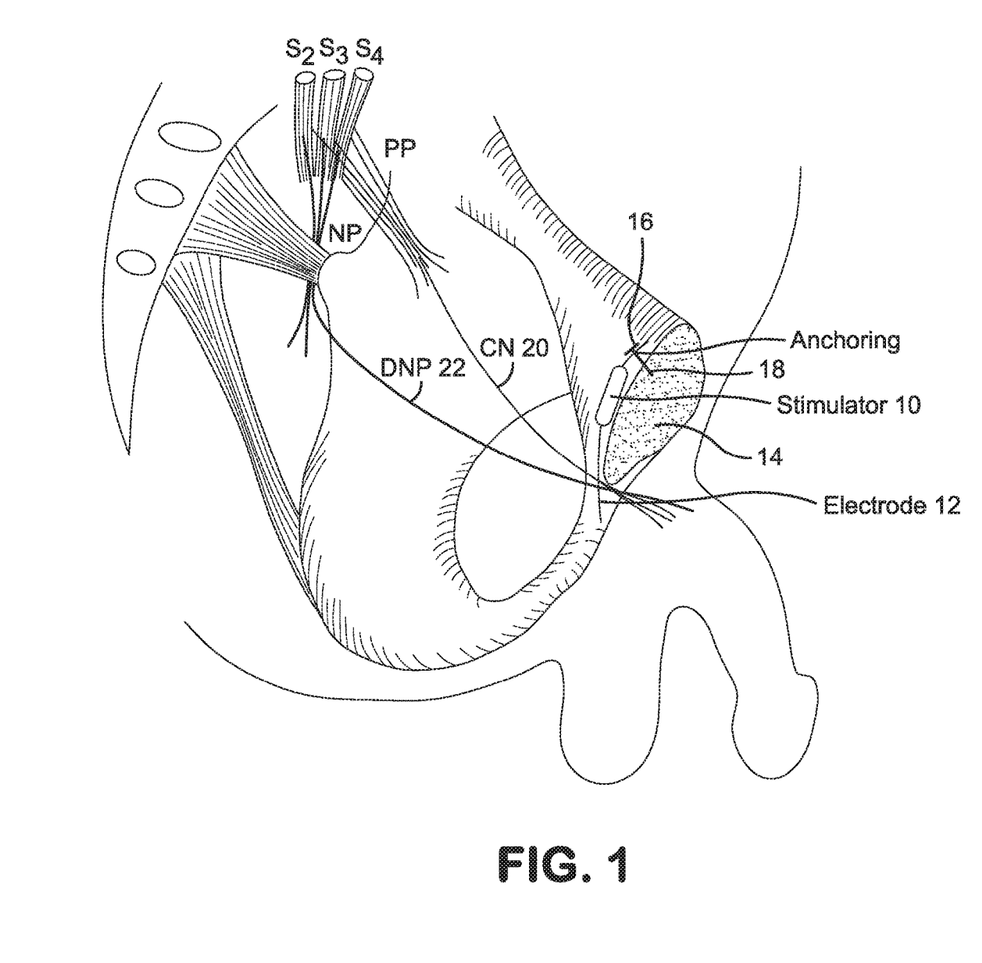
FIG. 1 is a side schematic view of an implantation according to the invention in a male patient.

FIG. 1 is a side schematic view showing implantation of a stimulator 10 with electrode 12 behind the pubic bone 14 of a patient. Stimulator 10 in this embodiment has an anchoring portion 16 which is shown anchored into pubic bone 14 in this case using a fastener 18, and electrode 12 extends from stimulator 10 to contact both the cavernous nerve 20, also marked CN in the drawing, and the dorsal nerve of the penis 22, also marked DNP in the drawing.

This placement is advantageous as set forth above, as a single electrode influencing both the CN and DNP can produce excellent results in restoring sexual function to male patients. Further, implanting the device in this location is a procedure which can be performed safely, and once implanted the device is in a good position to avoid and resist migration, and is shielded from outside forces or influences which could cause such migration and/or other damage.

Figure 2:
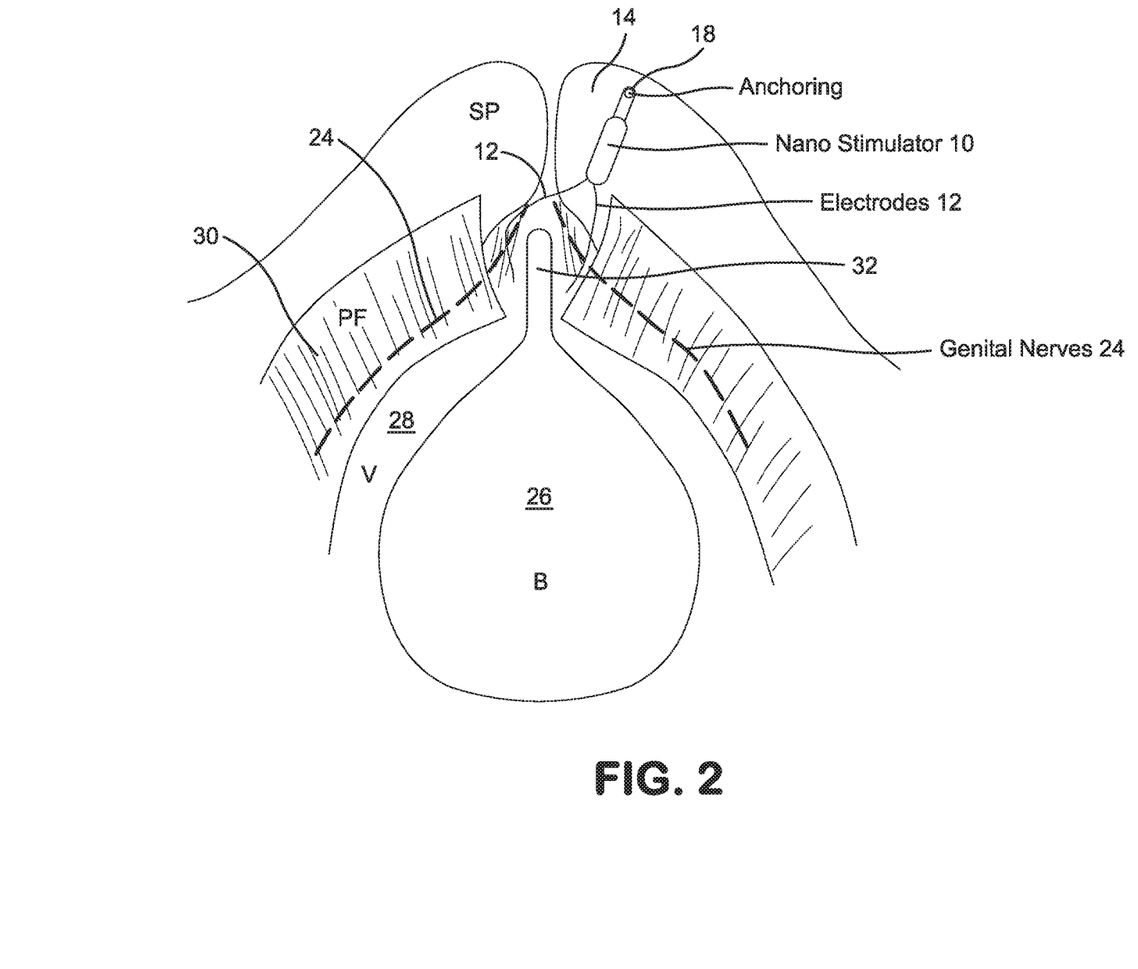
FIG. 2 is a side schematic view of an implantation according to the invention in a female patient.

FIG. 2 shows an endoscopic view of an implantation according to the invention in a female patient. As shown, a stimulator 10 is implanted again behind the pubic bone 14, for example using a fastener 18 as shown. In this case, it should be noted that stimulator 10 has two electrodes 12, which contact the genital nerves 24 of the patient to produce the desired effect. From an anatomical standpoint, FIG. 2 also shows bladder 26, vagina 28, pelvic floor 30 and urethra 32 of the patient.

It should be appreciated that this placement, as with the placement of FIG. 1, advantageously positions the stimulator and electrodes to contact the genital nerves such that the desired effect can be obtained, while the stimulator is implanted in a location which is safe during the procedure, and which resists migration or damage during use.

Figure 3:
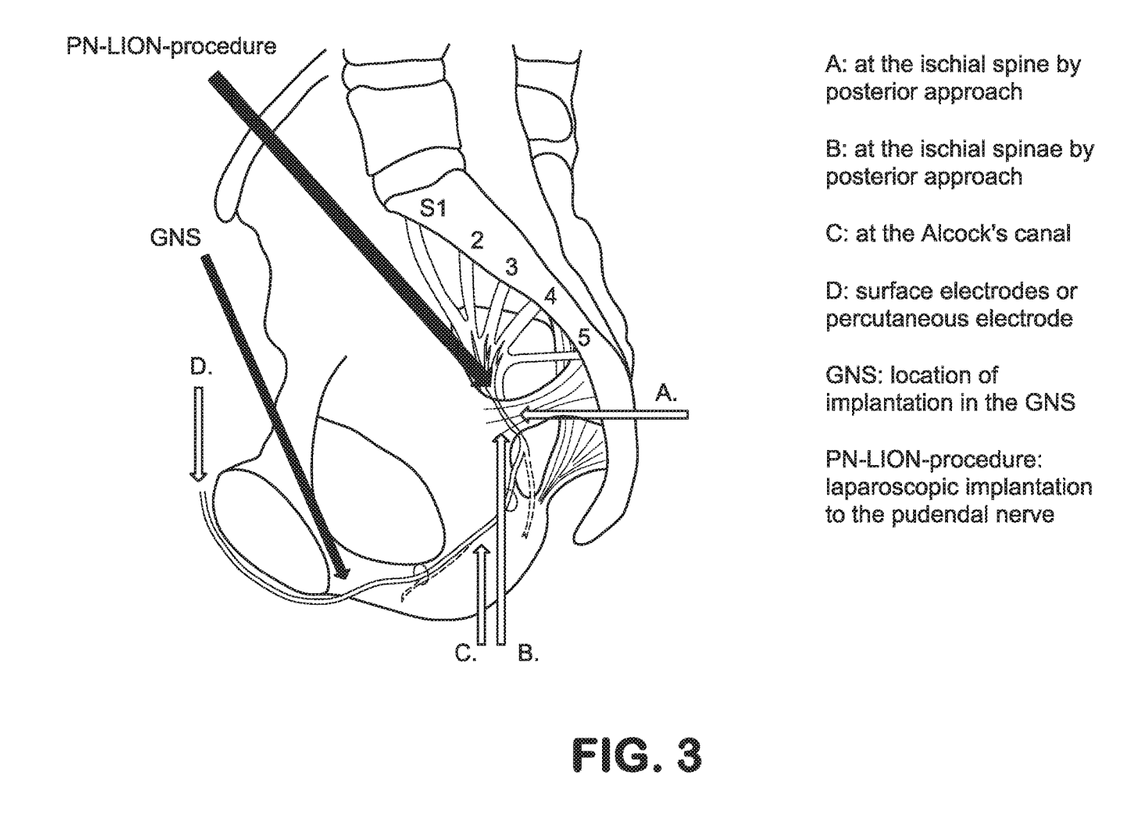
FIG. 3 is a schematic illustration of a number of different known implantation locations, as well as that of the present invention.

FIG. 3 is a summary of the various known procedures for implanting stimulators, as well as the method and implantation location according to the invention. Location A indicates the ischial spine location by an anterior approach. Location B indicates the ischial spine by a posterior approach. Location C indicates the Alcock's Canal. Location D indicates surface electrodes or percutaneous electrodes. Each of these approaches or procedures has disadvantages as discussed above.

Still referring to FIG. 3, PN-LION indicates a procedure of laparoscopic implantation of a stimulator to the pudendal nerve. Finally, GNS refers to the approach and location of implantation according to the present invention. This GNS position and line of approach is advantageous for the reasons set forth above.

The disclosure is directed to a method of implantation of a microstimulator (or other implantable medical device) to the dorsal nerve of the penis (or of the clitoris) and of the cavernous nerves together (collectively referred to as "Genital Nerves"). The GNS™—Genital Nerves Stimulation—system of the present invention is based on the implantation of a microstimulator system a few millimeters behind the pubic bone to both nerves (dorsal penis/clitoris nerves and cavernous nerves) bilaterally which nerves are close together at that location. The procedure can be performed either by a small skin incision hidden by the pubic hairs or by endoscopic approach (single port, laparoscopy, robotic surgery or the like) or by percutaneous suprapubic technique of implantation. While performing the procedure laparoscopically is particularly advantageous, it should be noted that the procedure can also be performed as a percutaneous and/or open surgery.

It is well known that the more selective a stimulation is, the better the effects, and in turn side effects (concomitant stimulation effects) are reduced. So for treatment of urinary and sexual dysfunctions, neuromodulation of the anterior branch of the pudendal nerve, which nerve is called "dorsal nerve of the penis/clitoris" or DNP has been found to be the nerve of choice to be stimulated.

According to the invention, the location of implantation can be reached by entering the retropubic space (Retzius space) from ventrally using a suprapubic minilaparotomic incision and digital expansion of the space of Retzius.

The approach to the nerve can also be obtained by transperitoneal approach. In the transperitoneal approach, a 10 mm primary trocar can be introduced umbilically. Two 5 mm secondary trocar can be introduced lateral to the inferior perigatsric, 5 cm above may be introduced suprapubically 3-4 cm above the symphysis pubis. A grasper is introduced through the right portal and grasps the parietal peritoneum above the level of bladder fold. The peritoneum is incised and then extended between the two umbilical ligaments with scissors or unipolar needle to open the Retzius space. The retropubic space is dissected bluntly with a suction irrigator. Staying close to the back of the pubic bone pushing the bladder, the vagina or the pelvic diaphragm in men, and urethra downward, the retropubic dissection is continued tracing from the back of symphysis pubis laterally limited to 3 cm lateral to the urethra. The medical device is implanted at that place perpendicularly to the course of the genital nerves, and finally fixed to the inferior or dorsal arch of the pubic bone. The medical device can be fixed by using suturing, stapling or screwing.

The exposure of the Retzius space can also be obtained by retroperitoneal approach. After making an incision in the subumbilical area, the anterior leaf of the rectus sheath is open. The space can be dissected using a balloon apparatus or by blunt dissection. This approach may be difficult if the patient has had prior abdominal surgery. In this or the transperitoneal approach discussed above, the approach is preferably made endoscopically, i.e. by means of an endoscope or the like.

The system is implanted within the protection of the pelvic cavity behind the pubic bone. The placement of the microstimulator is in the retropubic space, also known as the Retzius space, between the pubic symphyse, the urinary bladder and the pelvic diaphragm. The microstimulator can be fixed using suture, glue, screw, aggrafe, clip or the like, and is fixed to the pubic bone to thereby avoid risk of device migration or dislocation, and to protect it from external trauma breakage.

Figure 4:
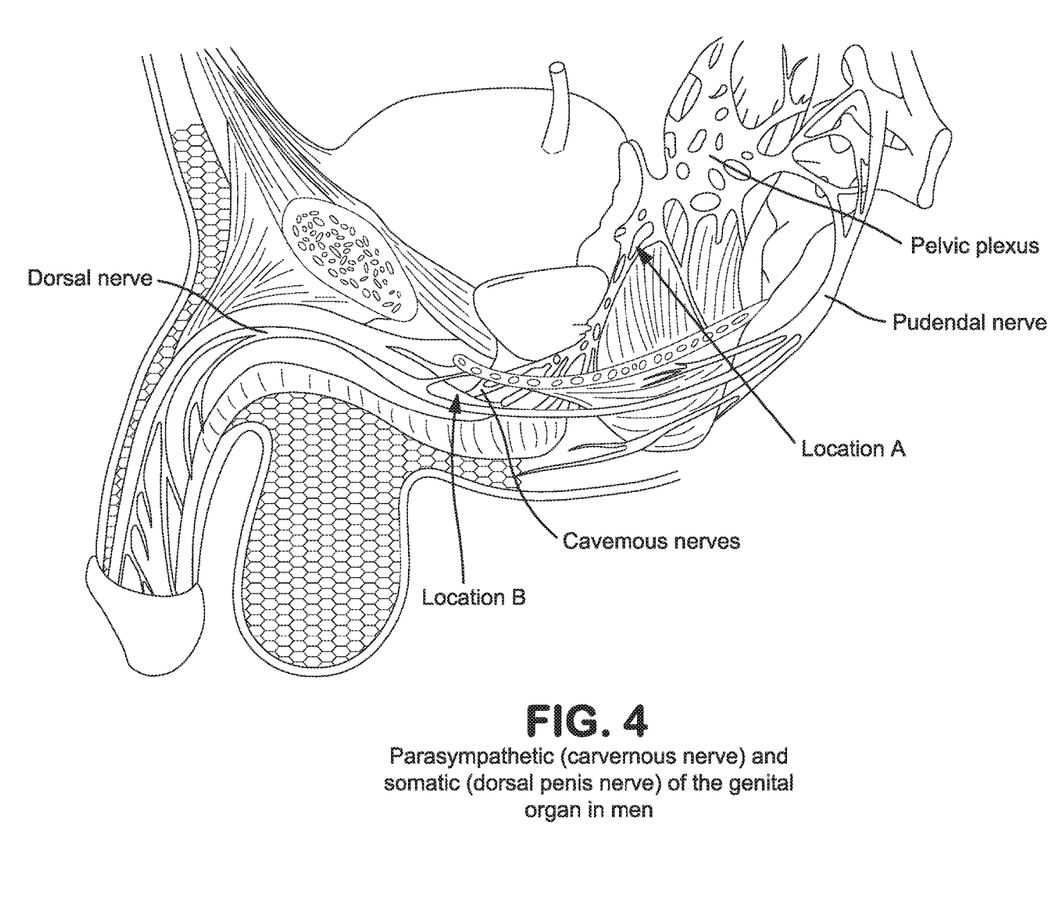
FIG. 4 shows Location A corresponding to a location of implantation according to the prior art, and Location B corresponding to the present invention.

Implantation behind the pubic bone enables easy placement of a stimulation device or other device to the genital nerves together where the nerves along the margin of the inferior ramus of the pubis, before they pierce the urogenital diaphragm (Ginger V A. Surgical Anatomy of the dorsal nerve of the clitoris. Neurourol Urodyn 2011, 30:412-6). At that place, implantation can be obtained in an avascular space, specifically the Retzius space as defined above, without need for dissection of the nerves. While the dorsal nerve of the penis emerges at the pelvic sidewall from the pudendal nerves, the cavernous nerves emerge from the sacral nerve roots and anastomose medially to the inferior hypogastric nerves. Implantation of electrodes at this location has been described in the past (FIG. 4, location A), but such procedure are laborious and difficult to reproduce. The only place where the dorsal nerves of the penis (or clitoris) and the cavernous nerves (parasympathetic nerves) are close together is exactly at this place behind the pubic bone where the nerves enter the genital organs together (FIG. 4, location B).

The ventral approach to the nerves avoids risk of injury of the deep dorsal vein and of the lateral venous plexus and the autonomous pelvic nerves.

The ventral approach enables the placement of only one microstimulator to the genital nerves bilaterally since at this location both sides are just separated by a few millimeters.

Electrical stimulation of the genital nerves may also provide therapy for patients experiencing urinary incontinence, urinary retention, bowel disorders, idiopathic and neurogenic overactive bladder, other pelvic floor disorders, and genital pain (especially neuropathic pudendal and genital pain).

Electrical stimulation of the genital nerves permits a selective control to the genital organs resulting in treatment of sexual dysfunctions by:
  increasing filling of the penis via dilatation of penile arteries to induce erection via stimulation of the cavernous nerves), preventing leakage via occlusion of penile veins,
producing a sustained reflex erection in men (via stimulation of the dorsal penis nerves), and
increasing sexual arousal and clitoris erection in women.

Using a remote controller, stimulation of the genital nerves may also induce sexual excitation that significantly improves sexual satisfaction and only the patient/user knows about the controlled stimulation.

In one embodiment, the invention provides a method for placing an implantable medical device to the somatic and parasympathetic (and in some conditions sympathetic) genital nerves for inducting and improving the quality of erection, but also for improving clitoris erection in women.

In one embodiment, the invention provides a method for placing an implantable medical device to the genital nerves for controlling over activity of the bladder and urge incontinence. Stimulation of the dorsal nerve of the penis has been demonstrated to be an effective method for treatment of OAB (Curr Urol Rep. 2012 October; 13(5):385-8. Dorsal genital nerve stimulation in patients with detrusor overactivity: a systematic review. Farag FF1, Martens F M, Rijkhoff N J, Heesakkers J P.)

In one embodiment, the invention provides a method for placing an implantable medical device to the genital nerves for controlling idiopathic fecal incontinence (Colorectal Dis. 2012 March; 14(3):349-55. Electrical stimulation of the dorsal clitoral nerve reduces incontinence episodes in idiopathic fecal incontinent patients: a pilot study. Worsøe J1, Fynne L, Laurberg S, Krogh K, Rijkhoff N J.)

In one embodiment, the invention provides a method for placing an implantable microstimulator, smaller than an almond, with an integral lead in a pelvis of a patient, the method comprising creating a path through the retropubic space (Retzius space), and placing the device via the path to the genital nerves on both sides with one multipolar lead, and with the device fixed to the pubic bone, so that the device is fixed adjacent to the nerve bilaterally. A hand-held remote controller, wirelessly communicated with the microstimulator, can be placed in front of the suprapubic area to provide on-demand patient-controlled GNS and recharge of the microstimulator. GNS settings are individualized and can be adjusted quickly by physicians using a programmer laptop, or the like. The skin incision required for GNS is much less noticeable than in classical generator implantation resulting in a visible scar with significant emotional and psychological impact, potentially affecting sexuality and bladder functions.

In one embodiment, the invention provides the implantation of a microstimulator with mounted stimulating electrodes directly on the microstimulator, which eliminates possible complications associated with the use of a lead.

In one embodiment, the invention provides a method for retropubic implantation of a medical device. This device is composed by a multipolar electrode lead that is connected to a generator (pacemaker) placed in the lower abdomen.

In another embodiment, the medical device to be implanted can be an "intelligent" microelectrode or a chip that permits stimulation of the nerves, and can be recharged and controlled from outside not just by a remote controller, but also by using a phone app or other communication and control protocol.

Neurophysiology and Anatomy of the Dorsal Nerve of the Penis/Clitoris

Figure 5:
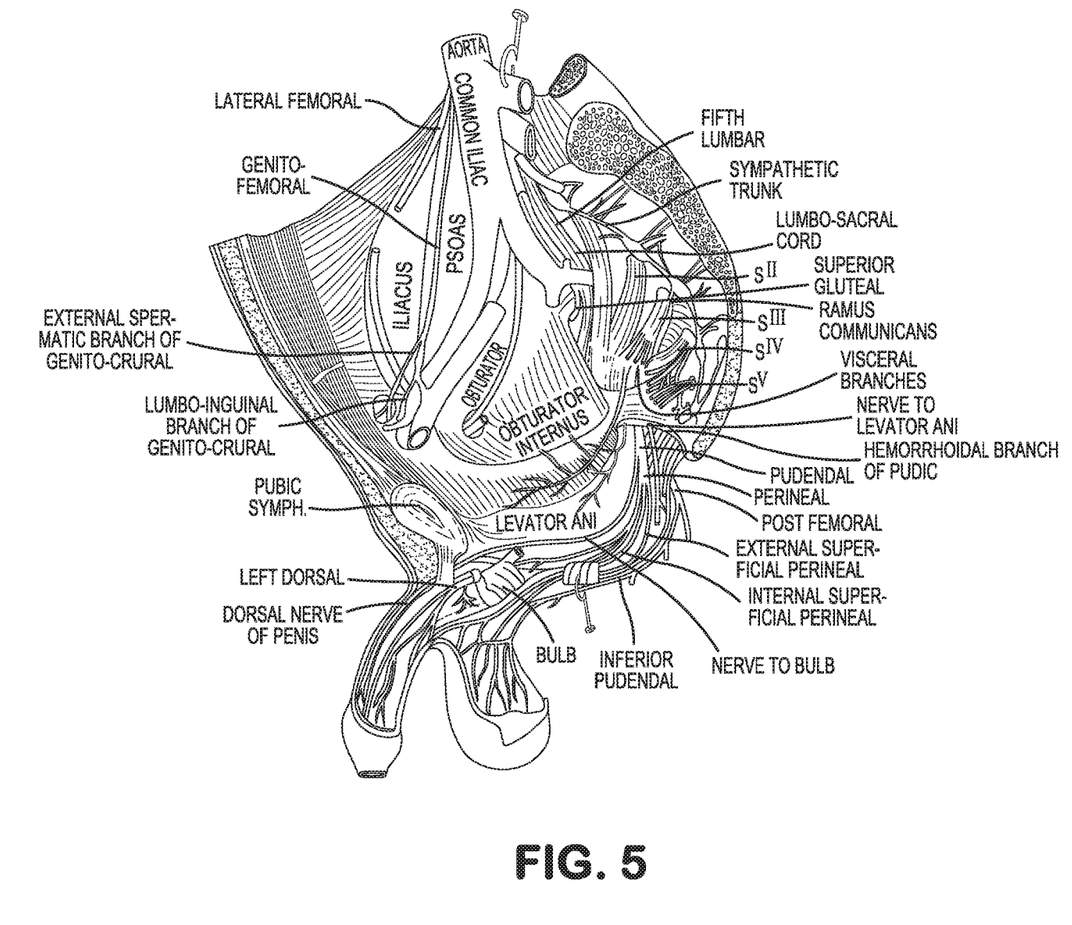
FIG. 5 is another illustration of the anatomy including the retropubic area of interest according to the invention.

The pudendal nerve is classically described as being derived from the second to fourth sacral segments and is composed of three main divisions, the dorsal nerve of the penis/clitoris, the perineal nerve, and the inferior rectal nerve. The dorsal nerve of the penis/clitoris arises close to the perineal nerve as the pudendal nerve exits Alcock's canal, a tunnel formed by a division of the obturator fascia along the lateral wall of the ischiorectal fossa. The dorsal nerve of the penis/clitoris travels along the ramus of the ischium and then along the margin of the inferior ramus of the pubis, until it pierces the urogenital diaphragm. Beneath the pubic arch, the nerves to the penis are an extension of the dorsal neurovascular bundle of the prostate. The nerves form 2 bundles following a path just under the pubic arch in close proximity to the bone, superior to the urethra and medial to the origin of the crural bodies. The nerve bundles join the corporeal bodies at the proximal origin, where the 2 crural bodies fuse together. At this point, perforating branches into the corporeal bodies from the cavernous nerves are documented. As the dorsal nerves join the dorsal aspect of the corporeal bodies, they immediately begin to fan out along the surface of the corporeal tissue to the junction of the urethral spongiosum. The nerve joins the penile shaft just beneath the inferior pubic ligament (The Urogenital System In Clemente C D, ed. Gray's Anatomy of the Human Body, 30th American edn. Philadelphia: Lea & Febiger, 1985; 1559-1564). This is illustrated in FIG. 5.

The crucial role of the dorsal nerve of the penis, or DNP in human erectile function was supported by Seftel et al. [Seftel A D, Resnick M I, Boswell M V. Dorsal nerve block for management of intraoperative penile erection. J Urol 1994; 151: 394-5], who showed that reflex erections could be abolished by anesthetizing the pudendal nerve. Investigations of the pudendal nerve and its influence on ejaculation have also defined the critical importance of the DNP in this response. The contraction of the bulbocavernosus muscle (BCM) is the predominant force for expelling semen from the bulbous urethra. Reflex contraction of this muscle after stimulation of the DNP has been documented with electrophysiological studies. Vibratory stimuli applied to the glans penis induced ejaculation in men with spinal cord injury, supporting the concept that the DNP is the principal source of afferent excitatory drive to the BCM and ejaculation.

Two populations of axons form the DNP, one with a constant course along the dorsum of the penis and then abundantly branching within the glans, and the other displaying a highly variable, although less extensive array of nerves along the penile shaft. For erectile function, the glans may act as a sensory organ, with transmission of sensory afferents through the DNP to the CNS. As the glans distends during erection, there is a resultant increase in glandular surface area. Stretching of the epithelial rete papillae exposes more sensory receptors to stimulation. The afferent impulses are conveyed to the intermediolateral cell column in the lumbar and sacral spinal cord, and to higher CNS centers such as the cortex. The resultant efferent impulses generated further propagate the sexual response by maintaining erection or initiating ejaculation. The abundant branching of the DNP within the glans supports the supposition that the glans acts as a sensory end-organ for sexual reflexes; animal studies also affirm this.

Some of the lateral fibers of the DNP penetrate the corpus spongiosum, the sinusoidal erectile tissue surrounding the urethra. The fibers of the DNP appear to penetrate the substance of the corpus spongiosum to innervate the urethral lumen. Pudendal innervation of the urethra had been previously documented in the cat but has not been confirmed in the human. As the function of the DNP is primarily somatosensory and dedicated exclusively to sexual reflexes, urethral sensation of the passage of seminal fluid during ejaculation may be the somatic afferent information necessary for sustaining reflex BCM contractions until the expulsion of all seminal fluid is complete.

The innervation of the penis is both autonomic (sympathetic and parasympathetic) and somatic (sensory and motor). From the neurons in the spinal cord and peripheral ganglia, the sympathetic and parasympathetic nerves merge to form the cavernous nerves, which enter the corpora cavernosa and corpus spongiosum to affect the neurovascular events during erection and detumescence. The somatic nerves are primarily responsible for sensation and the contraction of the bulbocavernosus and ischiocavernosus muscles.

The parasympathetic pathway arises from neurons in the intermediolateral cell columns of the second, third, and fourth sacral spinal cord segments. The preganglionic fibers pass in the pelvic nerves to the pelvic plexus, where they are joined by the sympathetic nerves from the superior hypogastric plexus. The cavernous nerves are branches of the pelvic plexus that innervate the penis. Other branches of the pelvic plexus innervate the rectum, bladder, prostate, and sphincters. The cavernous nerves are easily damaged during radical excision of the rectum, bladder, and prostate. A clear understanding of the course of these nerves is essential to the prevention of iatrogenic ED. Human cadaveric dissection revealed medial and lateral branches of the cavernous nerves (the former accompany the urethra and the latter pierce the urogenital diaphragm 4 to 7 mm lateral to the sphincter) and multiple communications between the cavernous and the dorsal nerves.

Stimulation of the pelvic plexus and the cavernous nerves induces erection, whereas stimulation of the sympathetic trunk causes detumescence. This clearly implies that the sacral parasympathetic input is responsible for tumescence and the thoracolumbar sympathetic pathway is responsible for detumescence. However, electrical stimulation of the sympathetic pathways to the penis also may produce erection (K-E Andersson, P Hedlund, P Alm2. Symptahetic pathways and adregernic innervation of the penis. Int. J. of Impotence Research 2000; 12, Suppl 1:5-12).

The somatosensory pathway originates at the sensory receptors in the penile skin, glans, and urethra and within the corpus cavernosum. In the human glans penis are numerous afferent terminations: free nerve endings and corpuscular receptors with a ratio of 10:1. The free nerve endings are derived from thin myelinated Aδ and unmyelinated C fibers and are unlike any other cutaneous area in the body. The nerve fibers from the receptors converge to form bundles of the dorsal nerve of the penis, which join other nerves to become the pudendal nerve. The latter enters the spinal cord via the S2-S4 roots to terminate on spinal neurons and interneurons in the central gray region of the lumbosacral segment. Activation of these sensory neurons sends messages of pain, temperature, and touch by means of spinothalamic and spinoreticular pathways to the thalamus and sensory cortex for sensory perception. The dorsal nerve of the penis used to be regarded as a purely somatic nerve; however, nerve bundles testing positive for nitric oxide synthase (NOS), which is autonomic in origin, have been demonstrated in the human by Burnett et al. and in the rat by Carrier and coworkers. Giuliano and associates have also shown that stimulation of the sympathetic chain at the L4-L5 level elicits an evoked discharge on the dorsal nerve of the penis and stimulation of the dorsal nerve evokes a reflex discharge in the lumbosacral sympathetic chain of rats. These findings clearly demonstrate that the dorsal nerve is a mixed nerve with both somatic and autonomic components that enable it to regulate both erectile and ejaculatory function.

The erection resulting from use of this invention, wherein tumescence of the glans and corpus spongiosum of the penis is evidenced, is natural and closer to the natural process than that effected by use of an intrapenile prosthesis. As further discussed above, the latter type of prosthesis, whether rigid, semi-rigid or inflatable, will normally cause destruction of substantially all of the erectile tissue within the corpora cavernosa of the penis. Further advantage of the invention resides in the fact that erection is non-permanent and will not hinder possible transurethral procedures, as does the rigid or semi-rigid prosthesis. Furthermore, this invention will not damage the erectile tissue within the corpora cavernosa of the penis which may become important should the patient later recover from the underlying disease affecting his impotency and again desire to regain his ability to achieve a totally natural erection.

The fibers innervating the penis (cavernous nerves) travel along the posterial lateral aspect of the seminal vesicle and prostate, then accompany the membranous urethra through the genitourinary diaphragm. Such nerves were further found to be located on the lateral aspect of the membranous urethra and gradually ascend to the one and eleven o'clock positions in the proximal bulbous urethra. Some of the fibers penetrate the tunica albuginea of the corpus spongiosum, whereas others spread over to the trifurcation of the terminal and internal pudendal artery and innervate the dorsal, deep and urethral arteries. Shortly prior to the point where the two corpora cavernosa merge, the cavernous nerves penetrate the tunica albuginea of the corpora, along with the deep artery and cavernous vein. The terminal branches of these nerves spread out to innervate the helicine arteries and the erectile tissue within the corpora cavernosa.

The invention claimed is:

1. A method for implanting a stimulator for genital nerves stimulation, comprising:
approaching genital nerves of a patient, defined as the dorsal nerve of the penis/clitoris (DNP), the cavernous nerves (CN) or both the DNP and CN, ventrally by way of the retropubic space to implant a stimulator to contact the genital nerves in this location, wherein the stimulator comprises a microstimulator implanted behind and fixed to the pubic bone and an electrode extending from the microstimulator to contact the genital nerves; and
controlling the stimulator to influence at least one of the genital nerves.

2. The method of claim 1, wherein the stimulator is implanted to contact the dorsal nerve and the cavernous nerve for sympathetic and parasympathetic genital innervation together.

3. The method of claim 1, wherein the stimulator is held in place by at least one of suturing, stapling and screwing.

4. The method of claim 1, wherein a single stimulator is implanted bilaterally to contact both the dorsal nerve and the cavernous nerve.

5. The method of claim 4, wherein the single stimulator is also implanted to contact the sympathetic genital nerves.

6. The method of claim 1, wherein the controlling step is carried out using a remote controller.

7. The method of claim 1, wherein the controlling step is carried out using a mobile device application.

8. The method of claim 1, wherein the approach step comprises entering the retropubic space ventrally using a suprapubic minilaparotomic incision and digital expansion of the space of Retzius.

* * * * *